(12) United States Patent
Donahue et al.

(10) Patent No.: US 11,840,726 B2
(45) Date of Patent: *Dec. 12, 2023

(54) MLH1 METHYLATION ASSAY

(71) Applicant: Quest Diagnostics Investments LLC, Secaucus, NJ (US)

(72) Inventors: Amber C. Donahue, San Juan Capistrano, CA (US); Feras Hantash, San Juan Capistrano, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 226 days.

This patent is subject to a terminal disclaimer.

(21) Appl. No.: 17/140,974

(22) Filed: Jan. 4, 2021

(65) Prior Publication Data
US 2021/0130871 A1 May 6, 2021

Related U.S. Application Data

(63) Continuation of application No. 15/568,502, filed as application No. PCT/US2016/028794 on Apr. 22, 2016, now Pat. No. 10,883,138.

(60) Provisional application No. 62/151,744, filed on Apr. 23, 2015.

(51) Int. Cl.
| | | |
|---|---|---|
| *C12Q 1/683* | (2018.01) | |
| *C12Q 1/68* | (2018.01) | |
| *C12Q 1/6886* | (2018.01) | |
| *C12N 9/16* | (2006.01) | |

(52) U.S. Cl.
CPC ............ *C12Q 1/683* (2013.01); *C12N 9/16* (2013.01); *C12Q 1/68* (2013.01); *C12Q 1/6886* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0026252 A1 | 2/2005 | Estes et al. |
| 2007/0092883 A1* | 4/2007 | Schouten ............ C12Q 1/6827 435/6.12 |
| 2007/0161013 A1 | 7/2007 | Hantash |
| 2010/0041049 A1 | 2/2010 | Smith et al. |
| 2013/0316339 A1 | 11/2013 | Ordway et al. |
| 2014/0242583 A1 | 8/2014 | Lu et al. |
| 2014/0357497 A1 | 12/2014 | Zhang et al. |

OTHER PUBLICATIONS

Perez-Carbonell (Journal of Molecular Diagnostics vol. 12 No. 4 Jul. 2010).*
GenBank Accession AY582799, Apr. 6, 2004.
GenBank Accession NG_007109, Mar. 30, 2012.
GenBank Accession US3845, Oct. 10, 1997.
GenBank NG_007109.2. *Homo sapiens* mutL Homolog 1 (MLH1), RefSeqGene (LRG_216) on chromosome 3 [online] Aug. 29, 2014 [retrieved Aug. 27, 2016]. Available on the internet: <URL: http://www.ncbi.nlm.nih.gov/nuccore/382544572?sat=119904819>.
International Search Report dated Aug. 29, 2016 in application No. PCT/US2016/028794.
MRC Holland. Salsa MLPA probemix P003-B2 MLH/1MSH2. [online] Jan. 2013 [retrieved Jul. 27, 2016]. Available on the internet: <URL: https://www.google.com/url?sa=t&rct=j&q=&esrc=s&source=web&cd=1&ved=0ahUKEwjqwNyuvJTOAhUBzGMKHSgMCsoQFggcMAA&url=http%3A%2f%2Fwww.mlpa.com%2FWebForms%2FWebFormDBData.aspx%3FFileOID%3DnLY3UfL4P5s%257C&usg=AFQjCNFTHFBFf_uaZBUI05aJ1dXTMpqP2w&sig2=aEdvX-6PNAORpfLieA6WuA&bbm=bv.128153897,d.cGc&cad=rja>.
Perez-Carbonell, Journal of Molecular Diagnostics, Jul. 2010, 12(4):498-405.

* cited by examiner

*Primary Examiner* — Amanda Haney
(74) *Attorney, Agent, or Firm* — Foley & Lardner LLP

(57) ABSTRACT

The present technology relates to methods for excluding Lynch syndrome as a possible diagnosis in patients suffering from colorectal cancers or endometrial cancers. These methods are based on detecting the methylation status of the MLH1 promoter 'C' region in colorectal and endometrial cancer patients using an improved and highly sensitive methylation-specific multiplex ligation-dependent probe amplification (MS-MLPA) assay.

20 Claims, 9 Drawing Sheets

Specification includes a Sequence Listing.

Figure 2A

| | Sample Group | Samples | MLH1 promoter 'C' region Ct | | deltaCt (+Hhal – no enz) |
|---|---|---|---|---|---|
| | | | No Enzyme | + Hhal | |
| Controls | Negative control | Unmethylated DNA (100ng) | 21.9 | 30.0 | 8.5 |
| | Positive control | Methylated DNA (100ng) | 22.4 | 22.5 | 0.1 |
| Possible Methylation-Positive Samples* | MSI+ FFPE | 18121T | 25.2 | 25.3 | 0.019 |
| | MSI+ FFPE | 139T | 27.0 | 26.155 | -0.8 |
| | BRAF V600E+ FFPE | 12646 | 27.5 | 29.6 | 2.1 |
| | MSI+ FFPE | 17191T | 28.9 | 28.4 | -0.5 |
| | BRAF V600E+ FFPE | 13225 | 24.6 | 27.6 | 3.0 |
| Likely Methylation-Negative Samples | Matched "N" FFPE of MSI-neg | 18132N | 25.3 | 27.6 | 2.3 |
| | BRAF V600E-neg FFPE | 14634T | 25.8 | 27.7 | 1.9 |
| | Matched "N" FFPE of BRAF V600E+ | 15844N | 25.6 | 29.3 | 3.7 |
| | BRAF V600E-neg FFPE | 17544 | 24.0 | 28.9 | 4.9 |
| | BRAF V600E-neg FFPE | 17213T | 25.5 | 30.9 | 5.4 |
| | BRAF V600E-neg FFPE | 16997 | 26.8 | 29.5 | 2.7 |
| | BRAF V600E-neg FFPE | 16489 | 24.7 | 26.5 | 1.8 |
| | Matched whole blood of MSI-neg | 17191WB | 23.1 | 35.1 | 12.0 |
| | Whole blood from JAK validation | 18671WB | 21.6 | 30.7 | 9.1 |

Figure 2B

| | Sample Group | Samples | MLH1 intron 14 Ct No Enzyme | + AluI | deltaCt (+AluI − no enz) |
|---|---|---|---|---|---|
| Controls | Negative control | Unmethylated DNA (100ng) | 22.6 | 28.6 | 6.0 |
| | Positive control | Methylated DNA (100ng) | 23.1 | 28.2 | 5.1 |
| Possible Methylation-Positive Samples* | MSI+ FFPE | 18121T | 25.4 | 27.2 | 1.8 |
| | MSI+ FFPE | 139T | 27.7 | 29.5 | 1.8 |
| | BRAF V600E+ FFPE | 12646 | 28.0 | 33.8 | 5.8 |
| | MSI+ FFPE | 17191T | 29.1 | 30.2 | 1.1 |
| | BRAF V600E+ FFPE | 13225 | 25.3 | 29.4 | 4.1 |
| Likely Methylation-Negative Samples | Matched "N" FFPE of MSI-neg | 18122N | 25.3 | 28.6 | 3.3 |
| | BRAF V600E-neg FFPE | 14634T | 26.3 | 27.8 | 2.4 |
| | Matched "N" FFPE of BRAF V600E+ | 15844N | 26.2 | 30.2 | 4.0 |
| | BRAF V600E-neg FFPE | 17544 | 24.7 | 27.8 | 3.1 |
| | BRAF V600E-neg FFPE | 17213T | 26.1 | 29.9 | 3.8 |
| | BRAF V600E-neg FFPE | 16997 | 27.2 | 29.5 | 2.3 |
| | BRAF V600E-neg FFPE | 16489 | 25.4 | 27.0 | 1.6 |
| | Matched whole blood of MSI-neg | 17191WB | 23.8 | 33.1 | 9.3 |
| | Whole blood from JAK validation | 18671WB | 22.3 | 32.0 | 9.7 |

Figure 2C

| | Sample Group | Samples | ACTB Ct No Enzyme | ACTB Ct Dual Digest | deltaCt (+enz − no enz) |
|---|---|---|---|---|---|
| Controls | Negative control | Unmethylated DNA (100ng) | 23.3 | 22.9 | -0.4 |
| Controls | Positive control | Methylated DNA (100ng) | 23.4 | 23.3 | -0.1 |
| Possible Methylation-Positive Samples* | MSI+ FFPE | 18121T | 25.5 | 25.5 | 0.0 |
| Possible Methylation-Positive Samples* | MSI+ FFPE | 139T | 28.0 | 26.8 | -1.2 |
| Possible Methylation-Positive Samples* | BRAF V600E+ FFPE | 12646 | 28.0 | 28.5 | 0.5 |
| Possible Methylation-Positive Samples* | MSI+ FFPE | 17191T | 28.4 | 27.9 | -0.5 |
| Possible Methylation-Positive Samples* | BRAF V600E+ FFPE | 13225 | 25.3 | 25.9 | 0.6 |
| Likely Methylation-Negative Samples | Matched "N" FFPE of MSI-neg | 18122N | 25.5 | 25.7 | 0.2 |
| Likely Methylation-Negative Samples | BRAF V600E-neg FFPE | 14634T | 26.3 | 26.1 | -0.2 |
| Likely Methylation-Negative Samples | Matched "N" FFPE of BRAF V600E+ | 15844N | 26.5 | 26.3 | -0.2 |
| Likely Methylation-Negative Samples | BRAF V600E-neg FFPE | 17544 | 24.8 | 25.0 | 0.2 |
| Likely Methylation-Negative Samples | BRAF V600E-neg FFPE | 17213T | 25.8 | 25.4 | -0.4 |
| Likely Methylation-Negative Samples | BRAF V600E-neg FFPE | 16997 | 27.5 | 27.4 | -0.1 |
| Likely Methylation-Negative Samples | BRAF V600E-neg FFPE | 16489 | 25.4 | 25.8 | 0.4 |
| Likely Methylation-Negative Samples | Matched whole blood of MSI-neg | 17191WB | 24.3 | 23.7 | -0.6 |
| Likely Methylation-Negative Samples | Whole blood from JAK validation | 18671WB | 23.1 | 22.5 | -0.6 |

Figure 4B

| Sample Group | Bisulfite Conversion 0= negative (unmethylated) 1=positive (methylated) | MeScore |
|---|---|---|
| BRAF V600E+ FFPE | 1 | 0.94 |
| BRAF V600E+ FFPE | 0 | 0.22 |
| BRAF V600E+ FFPE | 1 | 0.835 |
| BRAF V600E+ FFPE | 0 | 0.232 |
| BRAF V600E+ FFPE | 0 | 0.208 |
| BRAF V600E+ FFPE | 0 | -0.313 |
| MSI+ "T" FFPE | 0 | 0.011 |
| MSI+ "T" FFPE | 1 | 1.694 |
| BRAF V600E-neg FFPE | 1 | 0.751 |
| BRAF V600E-neg FFPE | 0 | -0.932 |
| BRAF V600E-neg FFPE | 0 | -0.528 |
| BRAF V600E-neg FFPE | 0 | -0.463 |
| BRAF V600E-neg FFPE | 0 | -0.086 |
| BRAF V600E-neg FFPE | 0 | 0.026 |
| BRAF V600E-neg FFPE | 0 | 0.035 |
| BRAF V600E-neg FFPE | 0 | 0.048 |
| BRAF V600E-neg FFPE | 0 | 0.285 |
| MSI+ matched "N" FFPE | 0 | 0.218 |
| MSI+ matched "N" FFPE | 0 | -0.452 |
| MSI+ matched "N" FFPE | 0 | 0.306 |
| MSI+ matched "N" FFPE | 0 | 0.097 |
| MSI-neg "T" FFPE | 0 | -0.046 |
| MSI-neg "T" FFPE | 0 | -0.662 |
| MSI-neg "T" FFPE | 0 | -0.088 |
| MSI-neg "T" FFPE | 0 | 0.207 |
| MSI-neg matched "N" FFPE | 0 | -0.221 |
| MSI-neg matched "N" FFPE | 0 | -0.338 |
| MSI-neg matched WB | 0 | -0.086 |
| JAK WB | 0 | -0.127 |
| JAK WB | 0 | -0.124 |
| BRAF V600E+ FFPE | 1 | 0.963 |
| BRAF V600E+ FFPE | 1 | 0.729 |
| BRAF V600E+ FFPE | 0 | -0.563 |
| BRAF V600E+ FFPE | 0 | 0.023 |
| BRAF V600E+ FFPE | 1 | 0.446 |
| MSI+ "T" FFPE | 1 | 0.392 |
| MSI+ "T" FFPE | 0 | -0.014 |
| MSI+ "T" FFPE | 1 | 1.184 |
| MSI+ "T" FFPE | 0 | -0.231 |
| BRAF V600E-neg FFPE | 0 | -0.407 |

Figure 4B (Cont.)

| Sample | Value | Score |
|---|---|---|
| BRAF V600E-neg FFPE | 0 | -0.37 |
| BRAF V600E-neg FFPE | 0 | -0.315 |
| BRAF V600E-neg FFPE | 0 | -0.301 |
| BRAF V600E-neg FFPE | 0 | 0.048 |
| BRAF V600E-neg FFPE | 0 | 0.053 |
| BRAF V600E-neg FFPE | 0 | 0.163 |
| MSI+ matched "N" FFPE | 0 | 0.214 |
| MSI+ matched "N" FFPE | 0 | -0.65 |
| MSI-neg "T" FFPE | 0 | -0.379 |
| MSI-neg "T" FFPE | 0 | 0.042 |
| MSI-neg "T" FFPE | 0 | 0.001 |
| MSI-neg "T" FFPE | 0 | -0.193 |
| MSI-neg "T" FFPE | 0 | -0.314 |
| MSI-neg matched "N" FFPE | 0 | -0.067 |
| MSI-neg matched "N" FFPE | 0 | 0.035 |
| MSI-neg matched "N" FFPE | 0 | 0.095 |
| MSI-neg matched WB | 0 | -0.265 |
| JAK WB | 0 | -0.141 |
| JAK WB | 0 | -0.124 |
| JAK WB | 0 | -0.134 |
| BRAF V600E+ FFPE | 0 | -0.021 |
| BRAF V600E+ FFPE | 1 | 0.79 |
| MSI+ "T" FFPE | 0 | -0.13 |
| MSI+ "T" FFPE | 1 | 1.009 |
| MSI+ "T" FFPE | 0 | -0.039 |
| MSI+ "T" FFPE | 0 | -0.006 |
| BRAF V600E-neg FFPE | 0 | -0.201 |
| BRAF V600E-neg FFPE | 0 | -0.189 |
| BRAF V600E-neg FFPE | 0 | -0.161 |
| BRAF V600E-neg FFPE | 0 | -0.116 |
| BRAF V600E-neg FFPE | 0 | -0.084 |
| BRAF V600E-neg FFPE | 0 | -0.049 |
| BRAF V600E-neg FFPE | 0 | 0.068 |
| BRAF V600E-neg FFPE | 0 | 0.076 |
| BRAF V600E-neg FFPE | 0 | 0.106 |
| BRAF V600E-neg FFPE | 0 | 0.128 |
| BRAF V600E-neg FFPE | 0 | 0.154 |
| BRAF V600E-neg FFPE | 0 | 0.231 |
| BRAF V600E-neg FFPE | 0 | 0.239 |
| MSI+ matched "N" FFPE | 0 | -0.053 |
| MSI+ matched "N" FFPE | 0 | 0.307 |
| MSI+ matched "N" FFPE | 0 | 0.014 |
| MSI+ matched "N" FFPE | 0 | -0.193 |
| MSI+ matched "N" FFPE | 1 | -0.257 |
| MSI-neg "T" FFPE | 0 | -0.073 |

Figure 4B (Cont.)

| | | |
|---|---|---|
| MSI-neg "T" FFPE | 0 | -0.482 |
| MSI-neg "T" FFPE | 0 | 0.094 |
| MSI-neg matched "N" FFPE | 0 | -0.522 |
| MSI-neg matched "N" FFPE | 0 | -0.593 |
| MSI-neg matched "N" FFPE | 0 | -0.553 |
| MSI+ "T" FFPE | 1 | 0.997 |
| MSI+ "T" FFPE | 1 | 4.558 |
| BRAF V600E+ FFPE | 1 | 0.684 |
| MSI+ "T" FFPE | 1 | 2.442 |
| BRAF V600E+ FFPE | 1 | 0.298 |
| MSI-neg matched "N" FFPE | 0 | 0.317 |
| BRAF V600E-neg FFPE | 0 | 0.213 |
| BRAF V600E+ matched "N" FFPE | 0 | 0.084 |
| BRAF V600E-neg FFPE | 0 | -0.627 |
| BRAF V600E-neg FFPE | 0 | -0.467 |
| BRAF V600E-neg FFPE | 0 | -0.17 |
| BRAF V600E-neg FFPE | 0 | -0.151 |
| MSI-neg matched WB | 0 | -0.318 |
| JAK WB | 0 | 0.063 |

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
aagcacctcc tccgctctgc                                                     20

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ctacaacaat ggtccaggga gcaca                                               25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgaacctgtg tctgccactg tgtg                                                24

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 4
aggaggagcc tgagaagc                                                   18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttgtgtgcc tctgctgag                                                  19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgagtgtgt gaacaagcag ag                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acctcatgct gctctcctta g                                               21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctcagcaa gtcttctgg                                                  19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctggtggga aagatgacc                                                  19

<210> SEQ ID NO 10
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 10
aggaggagcc tgagaagcgc caagcacctc ctccgctctg cgccagatca cctcagcaga        60
ggcacacaag                                                               70

<210> SEQ ID NO 11
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgagtgtgt gaacaagcag agctactaca acaatggtcc agggagcaca ggcacaaaag        60
ctaaggagag cagcatgagg t                                                  81

<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggctcagcaa gtcttctgga ctgtgaacct gtgtctgcca ctgtgtgctg ggtggtggtc        60
atctttccca ccagg                                                         75
```

MLH1 METHYLATION ASSAY

CROSS-REFERENCE TO RELATED APPLICATIONS

This application is a Continuation of U.S. application Ser. No. 15/568,502, which is the U.S. National Stage Application of PCT/US2016/028794, filed Apr. 22, 2016, which claims priority to U.S. Provisional Application No. 62/151,744, filed Apr. 23, 2015, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 4, 2021, is named sequence.txt and is 3,268 bytes in size.

TECHNICAL FIELD

The present technology relates to methods for excluding Lynch syndrome as a possible diagnosis in patients suffering from colorectal or endometrial cancers. These methods are based on detecting the methylation status of the MLH1 promoter in colorectal and endometrial cancer patients. Nucleic acid sequences that aid in the detection of the methylation status of the MLH1 promoter (such as primers and probes) are also disclosed.

BACKGROUND

The following description of the background of the present technology is provided simply as an aid in understanding the present technology and is not admitted to describe or constitute prior art to the present technology.

Alterations of DNA methylation patterns have been recognized as a common change in human cancers. Aberrant methylation of normally unmethylated CpG-rich areas, also known as CpG-islands, which are located in or near the promoter region of many genes, have been associated with transcriptional inactivation of important tumor suppressor genes, DNA repair genes, and metastasis inhibitor genes (Esteller, M. and Herman, J. G. *J Pathol.* 196:1-7 (2002); Esteller, M. *Lancet Oncol.* 4:351-358 (2003)). Therefore, detection of aberrant promoter methylation of cancer-related genes may be essential for diagnosis, prognosis and/or detection of metastatic potential of tumors. As the number of genes known to be hypermethylated in cancer is large and increasing, sensitive and robust multiplex methods for the detection of aberrant methylation of promoter regions are therefore desirable. In addition, the amount of DNA available for large-scale studies is often limited and of poor quality because the DNA is isolated from formalin fixed paraffin-embedded (FFPE) tissues that have been stored at room temperature for years.

Most current approaches for the detection of methylation are based on the conversion of unmethylated cytosine residues into uracil after sodium bisulfite treatment (Frommer et al., *Proc. Natl. Acad. Sci.* 89:1827-1831 (1992)), which are converted to thymidine during subsequent PCR. Thus, after bisulfite treatment, alleles that were originally methylated have different DNA sequences as compared to their corresponding unmethylated alleles. These differences can be exploited by several techniques such as, methylation-specific PCR (MSP), restriction digestion (COBRA), Methylight, direct sequencing, denaturing high performance liquid chromatography (DHPLC), nucleotide extension assays (MS-SnuPE), methylation-specific oligonucleotide (MSO) microarray, or HeavyMethyl (Frommer et al., supra; Cottrell et al., *Nucleic Acids Res.* 32: e10 (2004); Deng et al., *Nucleic Acids Res.* 30:E13 (2002); Eads et al., *Nucleic Acids Res.* 28, E32 (2000); Gitan et al., *Genome Res.* 12:158-164 (2002); Gonzalgo, M. & Jones, P. *Nucleic Acids Res.* 25:2529-2531 (1997); Herman et al., *Proc. Natl. Acad. Sci.* 93:9821-9826 (1996); Xiong, Z. & Laird, P., *Nucleic Acids Res.* 25, 2532-2534 (1997)). However, most of these methods are labor intensive and/or allow the study of the methylation status of only one gene at a time. In addition, most of these techniques are not suitable to study large numbers of paraffin-embedded tissue samples.

Commercially available Multiplex Ligation-dependent Probe Amplification (MLPA) kits are frequently used to detect methylation of the mismatch repair (MMR) genes including MLH1. The MLPA method (U.S. Pub. No. 2007/0092883) is based on the hybridization of hemi-probes to the target DNA, each pair of which is separated by only one or a few bases. Each hemi-probe is tagged with one of two universal sequences that are used as priming sites for PCR amplification. Hybridization is followed by ligation, and then amplification, using universal primers complementary to the tags included at the end of each hemi-probe. For methylation-specific MLPA (MS-MLPA), the ligation step is combined with a restriction endonuclease digestion step, using a methylation-sensitive enzyme that cleaves unmethylated DNA at a specific site. Accordingly, any hemi-probe: target dimer in which the target DNA is unmethylated will be digested, thereby failing to generate an intact sequence for exponential amplification.

Although the conventional MS-MLPA method obviates the need for bisulfite conversion, MLPA kits are extremely sensitive to factors such as inhibitors present in the input DNA, operator differences, incubation times, etc., and thus reproducibility of these conventional MS-MLPA assays is often questionable. Thus, there is a substantial need for more robust methods that effectively detect aberrant promoter methylation of cancer-related genes.

SUMMARY OF THE PRESENT TECHNOLOGY

In one aspect, the present disclosure provides a method for detecting methylation of a target nucleic acid sequence in the promoter of MLH1 in a sample comprising (a) incubating the sample comprising double-stranded genomic DNA with at least one methylation-sensitive restriction enzyme and at least one methylation-insensitive restriction enzyme, wherein (i) the methylation-sensitive restriction enzyme and the methylation-insensitive restriction enzyme are not isoschizomers of each other; (ii) the methylation-sensitive restriction enzyme cleaves the double-stranded genomic DNA at unmethylated recognition sites for the methylation-sensitive restriction enzyme, leaving methylated recognition sites for the methylation-sensitive restriction enzyme intact; (iii) the methylation-insensitive restriction enzyme cleaves the double-stranded genomic DNA at both methylated and unmethylated recognition sites for the methylation-insensitive restriction enzyme; (iv) the target nucleic acid sequence in the promoter of MLH1 in the sample comprises a recognition site for the methylation-sensitive restriction enzyme; and (v) a target nucleic acid sequence at the exon 14-intron 14 junction of MLH1 in the sample comprises a recognition site for the methylation-insensitive restriction enzyme; (b) incubating the sample with a plurality of probes for querying a plurality of target nucleic acids in the sample, wherein the plurality of probes comprises (i) a first locus specific probe comprising a first target specific region complementary to the target nucleic acid sequence in the promoter of MLH1; and (ii) a second locus specific probe comprising a second target specific region complementary to the target nucleic acid sequence at the exon 14-intron 14 junction of MLH1, wherein the first locus specific probe and second locus specific probe are detectably labelled; (c) hybridizing the plurality of probes to the plurality of target nucleic acids in the sample to form a plurality of hybridization complexes; (d) amplifying the plurality of hybridization complexes to produce a plurality of amplicons, wherein amplification is carried out with a plurality of primer sets comprising (i) a first forward primer comprising a region that is complementary to a nucleic acid sequence located 5' from the target nucleic acid sequence in the promoter of MLH1; (ii) a first reverse primer comprising a region that is complementary to a nucleic acid sequence located 3' from the target nucleic acid sequence in the promoter of MLH1; (iii) a second forward primer comprising a region that is complementary to a nucleic acid sequence located 5' from the target nucleic acid sequence at the exon 14-intron 14 junction of MLH1; and (iv) a second reverse primer comprising a region that is complementary to a nucleic acid sequence located 3' from the target nucleic acid sequence at the exon 14-intron 14 junction of MLH1; and (e) detecting the plurality of amplicons, wherein detecting an amplicon comprising the target nucleic acid sequence in the promoter of MLH1 indicates methylation of the target nucleic acid sequence in the promoter of MLH1 in the sample.

Additionally or alternatively, in some embodiments of the method, the plurality of probes further comprises a third locus specific probe comprising a third target specific region complementary to a target nucleic acid sequence at ACTB, wherein the target nucleic acid sequence at ACTB does not contain a recognition site for the methylation-sensitive restriction enzyme and the methylation-insensitive restriction enzyme and wherein the third locus specific probe is detectably labelled.

Additionally or alternatively, in some embodiments of the method, the first locus specific probe, the second locus specific probe and the third locus specific probe are detectably labelled with fluorophores. In some embodiments of the method, the fluorophores of the first locus specific probe, the second locus specific probe, and the third locus specific probe are distinct. In some embodiments of the method, the fluorophores are selected from the group consisting of FAM, CY5 and HEX.

In some embodiments of the method, the first locus specific probe comprises the sequence of 5' AAG-CACCTCCTCCGCTCTGC 3' (SEQ ID NO: 1) or a complement thereof. In some embodiments, the first locus specific probe comprises a 6-FAM fluorophore and a BHQ1 quencher moiety. Additionally or alternatively, in some embodiments of the method, the second locus specific probe comprises the sequence of 5' CTACAACAATGGTCCAGG-GAGCACA 3' (SEQ ID NO: 2) or a complement thereof. In some embodiments, the second locus specific probe comprises a HEX fluorophore and a BHQ1 quencher moiety. In some embodiments of the method, the third locus specific probe comprises the sequence of 5' TGAAC-CTGTGTCTGCCACTGTGTG 3' (SEQ ID NO: 3) or a complement thereof. In some embodiments, the third locus specific probe comprises a Cy5 fluorophore and a BHQ2 quencher moiety.

Additionally or alternatively, in some embodiments of the method, the plurality of primer sets further comprises a third forward primer comprising a region that is complementary to a nucleic acid sequence located 5' from the target nucleic acid sequence at ACTB; and a third reverse primer comprising a region that is complementary to a nucleic acid sequence located 3' from the target nucleic acid sequence at ACTB.

In some embodiments of the method, the first forward primer comprises the sequence of 5' AGGAGGAGCCT-GAGAAGC 3' (SEQ ID NO: 4) and the first reverse primer comprises the sequence of 5' CTTGTGTGCCTCTGCT-GAG 3' (SEQ ID NO: 5).

In some embodiments of the method, the second forward primer comprises the sequence of 5' CTGAGTGTGT-GAACAAGCAGAG 3' (SEQ ID NO: 6) and the second reverse primer comprises the sequence of 5' ACCT-CATGCTGCTCTCCTTAG 3' (SEQ ID NO: 7).

In some embodiments of the method, the third forward primer comprises the sequence of 5' GGCTCA-GCAAGTCTTCTGG 3' (SEQ ID NO: 8) and the third reverse primer comprises the sequence of 5' CCTGGTGG-GAAAGATGACC 3' (SEQ ID NO: 9).

In some embodiments of the method, the methylation-sensitive restriction enzyme is HhaI. In some embodiments of the method, the methylation-insensitive restriction enzyme is AluI.

In some embodiments of the method, the target nucleic acid sequence in the promoter of MLH1 corresponds to the MLH1 promoter 'C' region.

In some embodiments of the method, the sample is a FFPE tissue sample. In some embodiments of the method, the sample is whole blood (WB).

In some embodiments of the method, the sample is derived from a subject diagnosed with colorectal or endometrial cancer. In one embodiment, the subject diagnosed with colorectal or endometrial cancer is positive for the BRAF V600E mutation. In another embodiment, the subject diagnosed with colorectal or endometrial cancer is positive for microsatellite instability (MSI).

In some embodiments of the method, the sample is derived from a subject suspected of having Lynch syndrome. In some embodiments, the subject suspected of having Lynch syndrome displays tumors in one or more tissues selected from the group consisting of colon, rectum, endometrium, stomach, ovary, urinary tract, and small intestine. In one embodiment, the tumors of the subject suspected of having Lynch syndrome show a loss of MLH1 protein expression using immunohistochemical (IHC) methods. In other embodiments, the tumors of the subject suspected of having Lynch syndrome are positive for MSI.

In another aspect, the present disclosure provides methods for excluding Lynch syndrome as a possible diagnosis in a colorectal or endometrial cancer patient comprising interrogating the methylation status of the MLH1 promoter 'C' region in the colorectal or endometrial cancer patient using the nucleic acids and methods described herein, wherein methylation of the MLH1 promoter 'C' region indicates the absence of Lynch syndrome.

In some embodiments of the method, the patient displays tumors in one or more tissues selected from the group consisting of colon, rectum, endometrium, stomach, ovary, urinary tract, and small intestine. In some embodiments of the method, the tumor tissue of the patient displays loss of MLH1 protein expression by immunohistochemistry (IHC). In some embodiments of the method, the tumor tissue of the patient is positive for MSI. In some embodiments of the method, the tumor tissue of the patient is positive for the BRAF V600E mutation.

BRIEF DESCRIPTION OF THE DRAWINGS

FIG. 2A compares the real-time quantitative PCR data for the MLH1 promoter 'C' region amplicon for samples digested with HhaI and AluI against undigested control samples. FIG. 2B compares the real-time quantitative PCR data for the MLH1 intron 14 amplicon for samples digested with HhaI and AluI against undigested control samples.

FIG. 2C compares the real-time quantitative PCR data for the ACTB amplicon for samples digested with HhaI and AluI against undigested control samples. Because the BRAF V600E mutation is commonly associated with MLH1 promoter methylation in colorectal cancer (CRC) patients, V600E+ CRC patient samples were tested as possible positives for MLH1 promoter methylation. MSI+ samples were also tested as possible positives for MLH1 promoter methylation because MSI can occur as a result of either MLH1 germline mutation or MLH1 promoter methylation. As used herein, "matched N of MSI-negative" and "matched N of BRAF V600E+" refer to matched normal samples (e.g., normal tissue adjacent to the excised tumor) of MSI-negative and V600E+ CRC patients respectively. As used herein, "matched whole blood of MSI-negative" refers to a sample that was derived from a MSI-negative patient, where the matched normal sample provided along with the tumor tissue for screening was whole blood instead of adjacent normal tissue. As used herein, "whole blood from JAK validation" refers to a DNA sample that had been extracted from patient blood submitted for JAK2 testing. Both whole blood from JAK validation samples and matched whole blood of MSI-negative samples serve as possible negatives for MLH1 promoter methylation.

FIG. 4B shows the detailed results of the MeScore and bisulfite conversion data for each of the 104 samples depicted in FIG. 4A.

DETAILED DESCRIPTION

Figure 1:
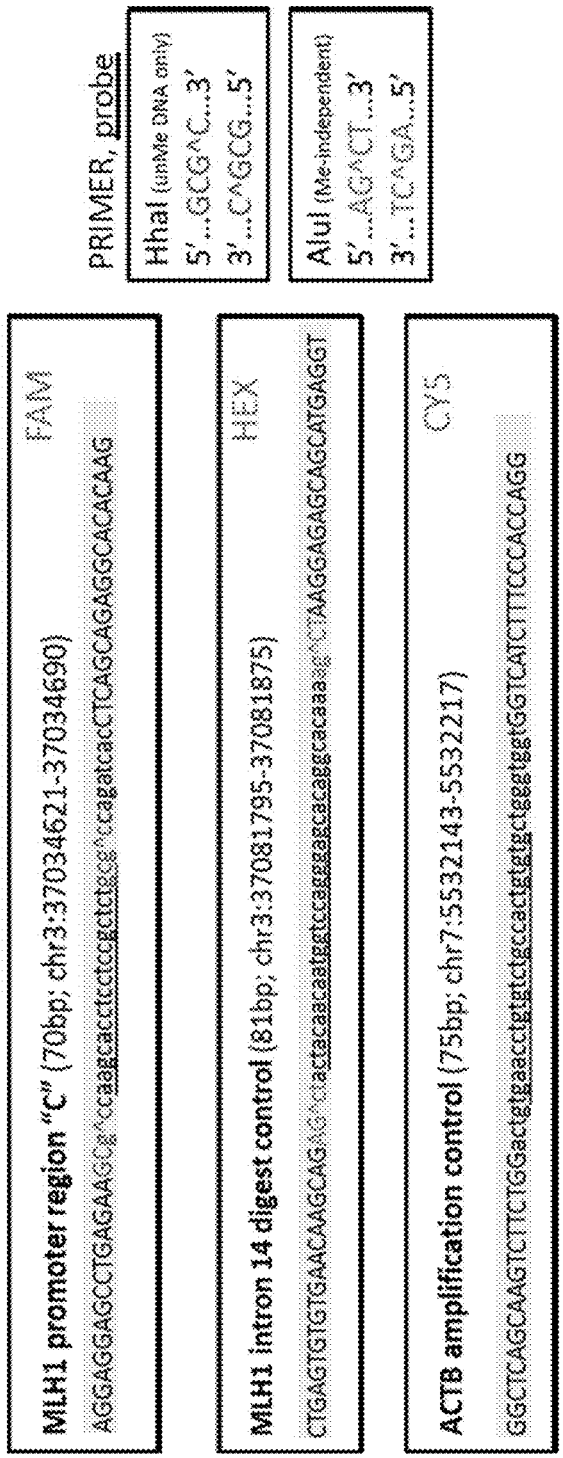
FIG. 1 shows the nucleic acid sequences of the MLH1 promoter 'C' region, MLH1 intron 14, and ACTB amplicons. HhaI and AluI recognition sites are highlighted in the relevant sequences. Primer sequences are depicted in uppercase font. Probe sequences are underlined. The primer/probe locations correspond to UCSC Genome Browser GRChv37/hg19 build coordinates. The three multiplex reactions (i.e., MLH1 promoter 'C' region (SEQ ID NO: 10), MLH1 intron 14 (SEQ ID NO: 11), and ACTB (SEQ ID NO: 12)) are performed with an undigested no-enzyme control and a HhaI-AluI dual-digest for each sample.

The present disclosure provides methods for excluding Lynch syndrome as a possible diagnosis in patients suffering from CRC or endometrial cancers. These methods are based on detecting the methylation status of the MLH1 promoter 'C' region in CRC and endometrial cancer patients using an improved and highly sensitive MS-MLPA assay. Nucleic acid sequences that aid in the detection of the methylation status of the MLH1 promoter 'C' region (such as primers and probes) are also disclosed.

DNA extracted from paraffin material is usually of poor quality and is notoriously difficult to digest with restriction endonucleases. Storage of tissues in formaldehyde solution results in extensive crosslinking of proteins to other proteins and to nucleic acids and in nucleic acid fragmentation (Grunau et al., Nucleic Acids Res. 29:E65 (2001); Lehmann U. & Kreipe H., Methods 25:409-418 (2001)). Paraffin embedding is a commonly used technique, which results in partial denaturation of the DNA, making digestion of the sample DNA very difficult.

Previous studies (U.S. Pub. No. 2007/0092883) have demonstrated that MS-MLPA methods involving the pre-digestion of genomic DNA with a CpG methylation-sensitive restriction endonuclease, followed by denaturation and hybridization with MS-MLPA probes is accompanied by several drawbacks. Specifically, the salt conditions required for restriction endonuclease digestion usually prevent the complete denaturation of the genomic CpG islands by a simple heating step. Furthermore, these methods preclude the analysis of most DNA samples derived from paraffin-embedded tissue, most probably due to partial denaturation of DNA that is extracted from most paraffin-embedded tissues.

Conventional MS-MLPA kits circumvent the abovementioned drawbacks by combining the ligation of MS-MLPA hemi-probes while hybridized to their target sequence with simultaneous digestion of these MS-MLPA hemi-probe-DNA complexes with methylation-sensitive restriction endonucleases. However, these kits do not account for inter-sample variations in the cleavage activities of the methylation-sensitive restriction endonucleases, making it difficult to determine whether a lack of digestion is truly due to protection of the sequence by methylation, or due to an inefficiency in the cleavage activity of the methylation-sensitive restriction enzyme within a given sample. Additionally, the performance of conventional MS-MLPA kits is impacted by a number of external factors such as inhibitors present in the input DNA, operator differences, incubation times, etc., thereby impeding an investigator's ability to replicate results.

The present disclosure provides methods for detecting aberrant methylation of the MLH1 promoter 'C' region using an improved and more robust MS-MLPA assay that monitors the actual performance of the methylation-sensitive restriction endonuclease in each individual test sample. In particular, the methods disclosed herein include the use of a methylation-insensitive restriction enzyme as an internal control for enzymatic digestion in each test sample. The methods of the present technology are useful in detecting MLH1 promoter methylation in genomic DNA derived from FFPE tissue samples, despite employing a step that involves digesting the genomic DNA of the sample with multiple restriction endonucleases. Accordingly, DNA degradation and partial DNA denaturation during embedding of the tissues or longtime storage do not appear to influence the accuracy of the results of the MLH1 methylation assay of the present technology. Further, the methods of the present technology are cost-effective and far less labor-intensive compared to other conventional methods for detecting methylation in genomic DNA samples (e.g., methylation-specific real-time PCR, bisulfite conversion, MRC-Holland MLPA kits etc.).

Definitions

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the terms "amplify" or "amplification" with respect to nucleic acid sequences, refer to methods that increase the representation of a population of nucleic acid sequences in a sample. Nucleic acid amplification methods, such as PCR, isothermal methods, rolling circle methods, etc., are well known to the skilled artisan. See, e.g., Saiki, "*Amplification of Genomic DNA*" in PCR PROTOCOLS, Innis et al., Eds., Academic Press, San Diego, Calif. 1990, pp 13-20; Wharam et al., *Nucleic Acids Res.* 2001 Jun. 1; 29(11):E54-E54; Hafner et al., *Biotechniques* 2001 April; 30(4):852-6, 858, 860 passim. Copies of a particular nucleic acid sequence generated in vitro in an amplification reaction are called "amplicons" or "amplification products".

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-S." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

"Detecting" as used herein refers to determining the presence of a methylated nucleic acid of interest (e.g., MLH1 promoter 'C' region) in a sample. Detection does not require the method to provide 100% sensitivity.

"Detectable label" as used herein refers to a molecule or a compound or a group of molecules or a group of compounds used to identify a nucleic acid or protein of interest. In some embodiments, the detectable label may be detected directly. In other embodiments, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable labels include but are not limited to spectroscopic, photochemical, biochemical, immunochemical, electromagnetic, radiochemical, or chemical means, such as fluorescence, chemifluorescence, or chemiluminescence, or any other appropriate means.

The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency than it would have in the absence of a closely positioned quencher moiety.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" can be an individual organism, a vertebrate, a mammal, or a human. In a preferred embodiment, the individual, patient or subject is a human.

As used herein, "isoschizomers" refer to pairs of restriction enzymes that are specific to the same recognition sequence. Isoschizomers are isolated from different strains of bacteria and therefore may require different reaction conditions. In some embodiments, only one out of a pair of isoschizomers can recognize both the methylated as well as unmethylated forms of recognition sites. In contrast, the other restriction enzyme can recognize only the unmethylated form of the recognition site. This property of some isoschizomers allows identification of the methylation status of the recognition site. For example, the restriction enzymes HpaII and MspI are isoschizomers, as they both recognize the unmethylated form of the sequence 5'-CCGG-3'. However, only MspI can recognize the methylated form of the recognition site.

As used herein, the terms "+LR" or "positive likelihood ratio" refer to the ratio between the probability of a positive test result given the presence of a methylated MLH1 promoter 'C' region in a sample and the probability of a positive test result given the absence of a methylated MLH1 promoter 'C' region in a sample.

As used herein, the terms "-LR" or "negative likelihood ratio" refer to the ratio between the probability of a negative test result given the presence of a methylated MLH1 promoter 'C' region in a sample and the probability of a negative test result given the absence of a methylated MLH1 promoter 'C' region in a sample.

The term "MLH1 promoter" as used herein refers to a segment of the MLH1 gene representing at least the first 250 nucleotides (nt) upstream from the translation start site of MLH1. In other embodiments, the promoter region may include the first 250 nt, first 300 nt, first 350 nt, first 400 nt, first 450 nt, first 500 nt, first 1 kb, first 5 kb, first 10 kb, first 15 kb, first 20 kb, first 21 kb or first 22 kb of sequence directly upstream of the start codon.

As used herein "MLH1 promoter 'C' region" refers to a small proximal region of the MLH1 promoter comprising the nucleotides located at positions 248 to 178 directly upstream from the translation start site. Methylation of the 8 CpG sites present in the MLH1 promoter 'C' region correlate with the loss of MLH1 expression in CRC or endometrial cancer.

The term "multiplex PCR" as used herein refers to amplification of two or more products which are each primed using a distinct primer pair.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. Probes can be labeled or unlabeled, or modified in any of a number of ways well known in the art. A probe may specifically hybridize to a target nucleic acid. Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be used to detect the presence or absence of a methylated target nucleic acid. Probes are typically at least about 10, 15, 20, 25, 30, 35, 40, 50, 60, 75, 100 nucleotides or more in length.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Forster or fluorescence resonance energy transfer ("FRET"). Quenching by FRET is generally used in TaqMan® probes while proximal quenching is used in molecular beacon and Scorpion™ type probes.

As used herein, the "deltaCt value (dCt)" for a particular amplicon (e.g., MLH1 promoter 'C' region, MLH1 intron 14, or ACTB) refers to the difference between the threshold cycle (Ct value) of the restriction enzyme-digested sample (e.g., HhaI-AluI dual digested sample) and the undigested control sample.

As used herein, the term "Ratio C" represents the actual amount of genomic DNA digestion by the methylation-sensitive restriction endonuclease (e.g., HhaI) normalized to the amount of total possible genomic DNA digestion in a given sample (which is measured by the activity of a methylation-insensitive restriction endonuclease, such as AluI). Ratio C is calculated using the formula below:

"Ratio $C$"=1−($MLH1$ promoter '$C$' region $dCt$/ $MLH1$ intron 14 $dCt$)

Accordingly, a small difference in the dCt values for the MLH1 promoter 'C' region and MLH1 intron 14 amplicons is indicative of complete digestion of the MLH1 promoter 'C' region, and thus reflects low levels of methylation at the MLH1 promoter 'C' region. Conversely, a large difference in the dCt values for the MLH1 promoter 'C' region and MLH1 intron 14 amplicons is indicative of incomplete digestion of the MLH1 promoter 'C' region, and thus reflects high levels of methylation at the MLH1 promoter 'C' region.

As used herein, the term "Ratio ACTB" represents the expected result for 100% methylation at the MLH1 promoter 'C' region factoring in any inter-well variability due to pipetting, etc. Ratio ACTB is calculated using the formula below:

"Ratio $ACTB$"=1−(|$ACTB\ dCt$|/$MLH1\ \text{intron}\ 14\ dCt$)

The "MeScore" of a sample is computed using the formula below:

"MeScore"="Ratio $C$"/"Ratio $ACTB$"

As used herein, the terms "restriction endonucleases" and "restriction enzymes" refer to bacterial enzymes each of which cleave double-stranded DNA at or near a specific nucleotide sequence known as a "restriction site", "recognition site", or "double-stranded recognition site."

As used herein, a "sample" refers to a substance that is being assayed for the presence of a methylated nucleic acid of interest (e.g., MLH1 promoter). Processing methods to release or otherwise make available a nucleic acid for detection are well known in the art and may include steps of nucleic acid manipulation. A biological sample may be a body fluid or a tissue sample. In some cases, a biological sample may consist of or comprise blood, plasma, sera, urine, feces, epidermal sample, vaginal sample, skin sample, cheek swab, sperm, amniotic fluid, cultured cells, bone marrow sample, tumor biopsies, and/or chorionic villi, cultured cells, and the like. Fixed or frozen tissues may also be used. Whole blood samples of about 0.5 to 5 ml collected with EDTA, ACD or heparin as anti-coagulant are suitable.

The term "sense strand" as used herein means the strand of double-stranded DNA (dsDNA) that includes at least a portion of a coding sequence of a functional protein. "Antisense strand" means the strand of dsDNA that is the reverse complement of the sense strand.

The term "sensitivity" as used herein in reference to the methods of the present technology means the probability that a test result will be positive when the MLH1 promoter 'C' region in a sample is methylated (true positive rate).

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

The term "specificity" as used herein in reference to the methods of the present technology means the probability that a test result will be negative when the MLH1 promoter 'C' region in a sample is not methylated (true negative rate).

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

"TaqMan® PCR detection system" as used herein refers to a method for real-time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

As used herein, the terms "target sequence" and "target nucleic acid sequence" refer to a specific nucleic acid sequence to be detected and/or quantified in the sample to be analyzed.

CRC, Endometrial Cancer, and Lynch Syndrome

CRC is one of the most common malignancies, representing the third most common cancer in men and the second in women worldwide. Endometrial cancer is the sixth most common cancer in women worldwide, with 320,000 new cases diagnosed in 2012.

Microsatellites are repeated DNA sequences that occur approximately every 50-100 Kb base pairs throughout the human genome. MSI is a hypermutable phenotype caused by the loss of DNA mismatch repair activity and is implicated in the development of CRC and endometrial cancer. MSI is detected in about 15% of all CRCs; 3% are of which are associated with Lynch syndrome and the other 12% are caused by sporadic, acquired hypermethylation of the promoter of the MLH1 gene, which occurs in tumors with the CpG island methylator phenotype. Colorectal tumors with MSI have distinctive features, including a tendency to arise in the proximal colon, lymphocytic infiltrate, and a poorly differentiated, mucinous or signet ring appearance. MSI is also present in endometrial cancer.

Hereditary nonpolyposis colon cancer (HNPCC), also known as Lynch syndrome, is an inherited cancer syndrome caused by a germline mutation in one of several genes involved in DNA mismatch repair (MMR), including MLH1, MSH2, MSH6 and PMS2. Lynch syndrome patients develop tumors at early ages, often between 20 and 30 years old and frequently exhibit multiple tumors, including those of the colon, rectum, endometrium, stomach, ovary, urinary tract, small intestine, and other sites, but no increase in the frequency of cancers of the breast, lung, or prostate.

There are several laboratory-based strategies that help establish the diagnosis of Lynch syndrome, including testing tumor tissue for the presence of MSI and loss of protein expression for any one of the MMR proteins by immunohistochemistry (IHC). However, the MSI tumor phenotype is not restricted to inherited cancer cases; approximately 20% of sporadic colon cancers are MSI. Thus, the presence of MSI does not distinguish between a somatic (sporadic)

and a germline (inherited) mutation, nor does it identify which gene is involved. IHC analysis, while helpful in identifying the affected gene, also does not distinguish between somatic and germline defects.

Defective MMR in sporadic colon cancer is most often due to abnormal MLH1 promoter hypermethylation (epigenetic silencing). The region of the MLH1 promoter in which methylation mediates gene silencing is the 3' end, close to the start codon (e.g., the 'C' region). The 5' end of the promoter is also prone to methylation. Methylation of the 5' end of the MLH1 promoter is not functionally relevant unless the methylation extends to the critical 3' region. Therefore, specific CpG residues are more important than others in mediating gene silencing. Importantly, most of the MSI-associated sporadic CRCs involve widespread CpG island promoter methylation (or CpG island methylator phenotype (CIMP) background), which is an important distinction from Lynch syndrome tumors.

A specific mutation in the BRAF gene (V600E) has been shown to be present in approximately 70% of tumors with hypermethylation of the MLH1 promoter. Importantly, the V600E mutation is rarely identified in cases with germline MLH1 mutations (e.g., Lynch syndrome). Thus, direct assessment of MLH1 promoter methylation status and testing for the BRAF V600E mutation are useful in distinguishing between a germline mutation and epigenetic/somatic inactivation of MLH1. Tumors that have the BRAF V600E mutation and demonstrate MLH1 promoter hypermethylation are almost certainly sporadic, whereas tumors that show neither are most often associated with an inherited disorder caused by a germline mutation (e.g., Lynch syndrome). The BRAF V600E mutation has been reported in CRC and endometrial cancers.

The likelihood of a germline mutation, e.g., a mutation present in Lynch syndrome, is very low in situations where the tumor demonstrates MLH1 promoter hypermethylation and the normal tissue is unmethylated. The likelihood of a germline mutation is high in those cases where the tumor and normal tissue lack MLH1 promoter hypermethylation.

Real-Time Quantitative PCR

Amplification of target nucleic acids can be detected by any of a number of methods well-known in the art such as gel electrophoresis, column chromatography, hybridization with a probe, sequencing, melting curve analysis, or "real-time" detection.

For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, Scorpion™ primer system and use of intercalating dyes for double-stranded nucleic acids.

In real-time quantitative PCR, the accumulation of amplification product is measured continuously in both standard dilutions of target DNA and samples containing unknown amounts of target DNA. A standard curve is constructed by correlating initial template concentration in the standard samples with the number of PCR™ cycles (Ct) necessary to produce a specific threshold concentration of product. In the test samples, target PCR™ product accumulation is measured after the same Ct, which allows interpolation of target DNA concentration from the standard curve.

In some embodiments, amplified nucleic acids are detected by hybridization with a specific probe. Probe oligonucleotides, complementary to a portion of the amplified target sequence may be used to detect amplified fragments. In some embodiments, hybridization may be detected in real time. Amplified nucleic acids for each of the target sequences may be detected simultaneously (i.e., in the same reaction vessel) or individually (i.e., in separate reaction vessels). For sequence-modified nucleic acids, the target may be independently selected from the top strand or the bottom strand. Thus, all targets to be detected may comprise top strand, bottom strand, or a combination of top strand and bottom strand targets.

One general method for real-time PCR uses fluorescent probes such as the TaqMan® probes, molecular beacons, and Scorpions. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

Real time PCR is performed using any suitable instrument capable of detecting the accumulation of the PCR amplification product. Most commonly, the instrument is capable of detecting fluorescence from one or more fluorescent labels. For example, real time detection on the instrument (e.g., an ABI Real-Time PCR System 7500® sequence detector) monitors fluorescence and calculates the measure of reporter signal, or Rn value, during each PCR cycle. The threshold cycle, or Ct value, is the cycle at which fluorescence intersects the threshold value. The threshold value can be determined by the sequence detection system software or manually.

TaqMan® probes (Heid et al., Genome Res. 6: 986-994, 1996) use the fluorogenic 5' exonuclease activity of Taq polymerase to measure the amount of target sequences in DNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al., 16 *Nature Biotechnology* 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase replicates a template on which a TaqMan® probe is bound, its 5' exonuclease activity cleaves the probe. This terminates the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye. If the quencher is an acceptor fluorophore, then accumulation of PCR product can be detected by monitoring the decrease in fluorescence of the acceptor fluorophore.

In some embodiments, the detectable label is a fluorophore. Suitable fluorescent moieties include but are not limited to the following fluorophores working individually or in combination: 4-acetamido-4'-isothiocyanatostilbene-2, 2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2-aminoethyl)aminonaphthalene-1-sulfonic acid (EDANS); 4-amino-N[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-dii sothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)amino fluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescem (TET); fiuorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rho damine isothiocyanate (TRITC); and VIC®.

Suitable quenchers are selected based on the fluorescence spectrum of the particular fluorophore. Useful quenchers include, for example, the Black Hole™ quenchers BHQ-1, BHQ 2, and BHQ-3 (Biosearch Technologies, Inc.), and the ATTO-series of quenchers (ATTO 540Q, ATTO 580Q, and ATTO 612Q; Atto-Tec GmbH).

MLH1 Methylation Assay of the Present Technology

The methods of the present technology are based on the principle that the target nucleic acid sequence in the promoter of MLH1 contains a restriction site recognized by a methylation-sensitive restriction endonuclease, such as HhaI, that is sensitive to cytosine methylation of at least one CpG site in its recognition sequence. Upon digestion with a methylation-sensitive restriction endonuclease, an amplification product of the target nucleic acid sequence in the promoter of MLH1 will only be obtained if the CpG site is methylated. The amplification product of the target nucleic acid sequence in the promoter of MLH1 is detected via real-time PCR.

It is to be understood that any methylated site present in a target nucleic acid in the promoter of MLH1 can be detected by the methods disclosed herein, as long as the site of interest (as part of a double-stranded recognition sequence) can be recognized by a methylation-sensitive restriction endonuclease (e.g., HhaI), cleaving the nucleic acid when the sequence of interest is unmethylated, and leaving the nucleic acid uncleaved when the sequence is methylated.

In addition to detecting the presence of a methylated target nucleic acid sequence in the promoter of MLH1 in a sample via methylation-sensitive restriction enzyme digestion in combination with real-time quantitative PCR, the assay evaluates the digestion of an alternate region of the MLH1 gene (e.g., at the exon-14-intron 14 junction) by a methylation-insensitive restriction enzyme that is not an isoschizomer of the methylation-sensitive restriction enzyme (e.g., AluI), as an internal control for complete enzymatic digestion within the sample.

Thus, the methods of the present technology account for variations in the cleavage activities of the methylation-sensitive restriction endonucleases from one sample to another, thereby allowing an investigator to discriminate between the lack of digestion being due to protection of the sequence by methylation, or due to an inefficiency in the cleavage activity of the restriction enzyme.

In some embodiments of the method, a sample comprising a control unmethylated target nucleic acid is provided to ensure the proper activity of the methylation-sensitive restriction enzyme and methylation-insensitive restriction enzyme.

In some embodiments of the method, a control sample lacking both the methylation-sensitive restriction enzyme and methylation-insensitive restriction enzyme is included in order to check the maximum performance of the system. In such situations, all the target nucleic acids, regardless of their methylation status, will be amplified.

In some embodiments, a sample comprising genomic DNA is split into two aliquots, one of which is simultaneously digested with both a methylation-sensitive restriction enzyme and a methylation-insensitive restriction enzyme, while the other is incubated in digestion buffer lacking either restriction enzyme.

In some embodiments of the method, amplification of a region (e.g., ACTB) that lacks restriction sites for both the methylation-sensitive restriction enzyme and methylation-insensitive restriction enzyme is included as an internal control for the complete absence of enzymatic digestion.

In some embodiments of the method, the level of methylation of a target nucleic acid sequence in the promoter of MLH1 in a sample is quantified by computing the MeScore as defined herein.

Thus according to the methods of the present technology, if the MLH1 promoter 'C' region is methylated (and thus protected from digestion by the methylation-sensitive restriction endonuclease), the MLH1 promoter 'C' region amplicon will be detected, and yield a Ct value that is comparable to that observed in the corresponding undigested control sample that lacks both the methylation-sensitive restriction enzyme and methylation-insensitive restriction enzyme.

However, if the targeted CpG sites in the MLH1 promoter 'C' region are unmethylated, the MLH1 promoter 'C' region will be cleaved at or near the recognition sites for the methylation-sensitive restriction endonuclease, thereby reducing the amount of intact target nucleic acid sequence available for the amplification and detection of the MLH1 promoter 'C' region amplicon. In light of the high sensitivity of real-time quantitative PCR assays, it is understood that any unmethylated DNA left intact after being subjected to methylation-sensitive restriction endonuclease digestion will be amplified and detected. Thus the resulting MLH1 promoter 'C' region amplicon would yield a higher Ct value relative to that observed in the corresponding undigested control sample that lacks both the methylation-sensitive restriction enzyme and methylation-insensitive restriction enzyme.

A heterogeneous positive sample containing a large fraction of normal DNA mixed with tumor DNA, and therefore a mixture of methylated and unmethylated DNA in the MLH1 promoter 'C' region, would thus undergo an intermediate level of digestion at the targeted CpG sites, and yield an intermediate upward shift in Ct value.

The methods disclosed herein require that the Ct values for the MLH1 promoter 'C' region amplicon in a given sample be compared to the corresponding Ct values for the MLH1 intron 14 amplicon (see below) in the same sample to confirm that the detected signal for the MLH1 promoter 'C' region is due to protection of the sequence by methylation (a true positive), rather than an inefficiency in the cleavage activity of the methylation-sensitive restriction enzyme within a sample. For example, the presence of carryover of inhibitory agents in the input DNA of a methylation-negative sample may result in a smaller-than-average shift in Ct value for the MLH1 promoter 'C' region amplicon, which would suggest the presence of methylation (a false-positive call). Similarly, a high degree of genomic DNA fragmentation in a sample would also lead to false positive calls. The methods disclosed herein overcome these drawbacks by assaying the enzymatic activity of a methylation-insensitive restriction endonuclease as an internal reference for enzymatic digestion within the sample.

The MLH1 intron 14 region (located at the exon-14-intron 14 junction) contains a restriction site recognized by the methylation-insensitive restriction enzyme (e.g., AluI). The MLH1 intron 14 region in a sample will be cleaved at or near the recognition sites for the methylation-insensitive restriction endonuclease, regardless of the methylation status of the region. Digestion of the MLH1 intron 14 region thus reduces the amount of intact target nucleic acid sequence available for the amplification and detection of the MLH1 intron 14 amplicon.

Any intact target nucleic acid sequence in the MLH1 intron 14 region that persists after digestion with the methylation-insensitive restriction enzyme will be amplified and detected. Thus the resulting MLH1 intron 14 amplicon would yield a higher Ct value relative to that observed in the corresponding undigested control sample that lacks both the methylation-sensitive restriction enzyme and methylation-insensitive restriction enzyme.

In some embodiments of the method, amplification of a region (e.g., ACTB) that lacks restriction sites for both the methylation-sensitive restriction enzyme and methylation-insensitive restriction enzyme is included as an internal control for the complete absence of enzymatic digestion. Thus, the ACTB amplicon in the sample digested with both the methylation-sensitive restriction enzyme and methylation-insensitive restriction enzyme will yield a Ct value that is nearly identical to that observed in the corresponding undigested control sample that lacks both the methylation-sensitive restriction enzyme and methylation-insensitive restriction enzyme. In some embodiments of the method, the deltaCt value for the ACTB amplicons between the undigested and digested samples accounts for any intra-sample variability, such as those created by pipetting errors, etc.

In some embodiments of the method, the deltaCt value for the MLH1 promoter 'C' region amplicon in a given sample is compared to the corresponding deltaCt value for the ACTB amplicon in the same sample, wherein a low difference in deltaCt values between the MLH1 promoter 'C' region amplicon and the ACTB amplicon is indicative of high levels of methylation.

In another embodiment, a plurality of different methylation-sensitive restriction enzymes can be used in a single or in separate reactions to detect multiple methylated sites within a single or a plurality of target nucleic acid sequences in the promoter of MLH1 in a sample, wherein the different methylation-sensitive restriction enzymes are not isoschizomers of each other.

In another aspect, the present disclosure provides robust methods for detecting aberrant methylation of the MLH1 promoter in DNA samples extracted from FFPE tissue.

Identification of the Risk of Lynch Syndrome in Patients Suffering from CRC or Endometrial Cancer The methods disclosed herein can provide useful diagnostic information when evaluating a patient suspected of having Lynch syndrome, especially when testing is performed in conjunction with HNPCC/Hereditary Nonpolyposis Colorectal Cancer (HNPCC) Screen, which includes MSI and IHC studies.

The described methods for detecting the presence of aberrant methylation of the MLH1 promoter in a sample may be used for determining whether a patient suffering from CRC or endometrial cancer should be diagnosed with Lynch syndrome. In some embodiments of the method, the tumor tissue of the patient displays loss of MLH1 protein expression by immunohistochemistry (IHC). In some embodiments of the method, the tumor tissue of the patient is positive for MSI. In some embodiments of the method, the tumor tissue of the patient is positive for the BRAF V600E mutation.

In one embodiment, the present technology provides a method for excluding Lynch syndrome as a possible diagnosis in a CRC or endometrial cancer patient comprising (a) incubating a double-stranded genomic DNA sample obtained from the patient with at least one methylation-sensitive restriction enzyme and at least one methylation-insensitive restriction enzyme, wherein (i) the methylation-sensitive restriction enzyme and the methylation-insensitive restriction enzyme are not isoschizomers of each other; (ii) the methylation-sensitive restriction enzyme cleaves the double-stranded genomic DNA at unmethylated recognition sites for the methylation-sensitive restriction enzyme, leaving methylated recognition sites for the methylation-sensitive restriction enzyme intact; (iii) the methylation-insensitive restriction enzyme cleaves the double-stranded genomic DNA at both methylated and unmethylated recognition sites for the methylation-insensitive restriction enzyme; (iv) a target nucleic acid sequence in the promoter of MLH1 in the sample comprises a recognition site for the methylation-sensitive restriction enzyme; and (v) a target nucleic acid sequence at the exon 14-intron 14 junction of MLH1 in the sample comprises a recognition site for the methylation-insensitive restriction enzyme; (b) incubating the sample with a plurality of probes for querying a plurality of target nucleic acids in the sample, wherein the plurality of probes comprises (i) a first locus specific probe comprising a first target specific region complementary to the target nucleic acid sequence in the promoter of MLH1; and (ii) a second locus specific probe comprising a second target specific region complementary to the target nucleic acid sequence at the exon 14-intron 14 junction of MLH1, wherein the first locus specific probe and second locus specific probe are detectably labelled; (c) hybridizing the plurality of probes to the plurality of target nucleic acids in the sample to form a plurality of hybridization complexes; (d) amplifying the plurality of hybridization complexes to produce a plurality of amplicons, wherein amplification is carried out with a plurality of primer sets comprising (i) a first forward primer comprising a region that is complementary to a nucleic acid sequence located 5' from the target nucleic acid sequence in the promoter of MLH1; (ii) a first reverse primer comprising a region that is complementary to a nucleic acid sequence located 3' from the target nucleic acid sequence in the promoter of MLH1; (iii) a second forward primer comprising a region that is complementary to a nucleic acid sequence located 5' from the target nucleic acid sequence at the exon 14-intron 14 junction of MLH1; and (iv) a second reverse primer comprising a region that is complementary to a nucleic acid sequence located 3' from the target nucleic acid sequence at the exon 14-intron 14 junction of MLH1; and (e) detecting the plurality of amplicons, wherein detecting an amplicon comprising the target nucleic acid sequence in the promoter of MLH1 indicates methylation of the target nucleic acid sequence in the promoter of MLH1 in the sample and the absence of Lynch syndrome in the patient.

Additionally or alternatively, in some embodiments of the method, the plurality of probes further comprises a third locus specific probe comprising a third target specific region complementary to a target nucleic acid sequence at ACTB, wherein the target nucleic acid sequence at ACTB does not contain a recognition site for the methylation-sensitive restriction enzyme and the methylation-insensitive restriction enzyme and wherein the third locus specific probe is detectably labelled.

Additionally or alternatively, in some embodiments of the method, the first locus specific probe, the second locus specific probe and the third locus specific probe are detectably labelled with fluorophores. In some embodiments of the method, the first locus specific probe, the second locus specific probe, and the third locus specific probe are labelled with a distinct fluorophore to allow discrimination between the detected amplicons. In some embodiments of the method, the fluorophores are selected from the group consisting of FAM, CY5 and HEX.

In some embodiments of the method, the first locus specific probe comprises the sequence of 5' AAGC-ACCTCCTCCGCTCTGC 3' (SEQ ID NO: 1) or a complement thereof. In some embodiments, the first locus specific probe comprises a 6-FAM fluorophore and a BHQ1 quencher moiety. Additionally or alternatively, in some embodiments of the method, the second locus specific probe comprises the sequence of 5' CTACAACAATGGTCCAGG-GAGCACA 3' (SEQ ID NO: 2) or a complement thereof. In some embodiments, the second locus specific probe comprises a HEX fluorophore and a BHQ1 quencher moiety. In some embodiments of the method, the third locus specific probe comprises the sequence of 5' TGAACCTGTG-TCTGCCACTGTGTG 3' (SEQ ID NO: 3) or a complement thereof. In some embodiments, the third locus specific probe comprises a Cy5 fluorophore and a BHQ2 quencher moiety.

Additionally or alternatively, in some embodiments of the method, the plurality of primer sets further comprises a third forward primer comprising a region that is complementary to a nucleic acid sequence located 5' from the target nucleic acid sequence at ACTB; and a third reverse primer comprising a region that is complementary to a nucleic acid sequence located 3' from the target nucleic acid sequence at ACTB.

In some embodiments of the method, the first forward primer comprises the sequence of 5' AGGAGGAGCCT-GAGAAGC 3' (SEQ ID NO: 4) and the first reverse primer comprises the sequence of 5' CTTGTGTGCCTCTGCT-GAG 3' (SEQ ID NO: 5).

In some embodiments of the method, the second forward primer comprises the sequence of 5' CTGAGTGTGT-GAACAAGCAGAG 3' (SEQ ID NO: 6) and the second reverse primer comprises the sequence of 5' ACCT-CATGCTGCTCTCCTTAG 3' (SEQ ID NO: 7).

In some embodiments of the method, the third forward primer comprises the sequence of 5' GGCTCAGCA-AGTCTTCTGG 3' (SEQ ID NO: 8) and the third reverse primer comprises the sequence of 5' CCTGGTGGGAAA-GATGACC 3' (SEQ ID NO: 9).

In some embodiments of the method, the methylation-sensitive restriction enzyme is HhaI. In some embodiments of the method, the methylation-insensitive restriction enzyme is AluI.

In some embodiments of the method, the target nucleic acid sequence in the promoter of MLH1 corresponds to the MLH1 promoter 'C' region.

In some embodiments of the method, the sample is a FFPE tissue sample. In some embodiments of the method, the sample is WB.

The methods disclosed herein can also be used to determine whether a patient suffering from CRC or endometrial cancer is a suitable candidate for Lynch syndrome therapies. Lynch syndrome therapies include colectomy, oophorectomy and hysterectomy.

In certain embodiments, the present disclosure provides methods for determining whether a patient suffering from CRC or endometrial cancer is a suitable candidate for Lynch syndrome therapies comprising interrogating the methylation status of the MLH1 promoter 'C.' region in the CRC or endometrial cancer patient using the nucleic acids and methods described herein, wherein methylation of the MLH1 promoter 'C' region indicates that the patient is not a suitable candidate for Lynch syndrome therapies.

Kits

The present disclosure also provides kits for detecting the methylation status of the MLH1 promoter via the improved MS-MLPA methods disclosed herein. Kits of the present technology comprise one or more target-specific nucleic acid probes as disclosed herein (e.g., probes specific to MLH1 promoter C region, MLH1 intron 14 or ACTB), alone or in combination with one or more primer pairs as disclosed herein, for amplification and detection of methylated target nucleic acid sequences within the genomic DNA of a given sample.

In some embodiments, the kits provide a target-specific nucleic acid probe comprising at least a part of a single stranded sequence constituting one of the strands of a double stranded recognition site of a methylation-sensitive restriction enzyme. In some embodiments, the target-specific nucleic acid probe comprising at least a part of a single stranded sequence constituting one of the strands of a double stranded recognition site of a methylation-sensitive restriction enzyme comprises the sequence 5' AAGCACCT-CCTCCGCTCGC 3' (SEQ ID NO: 1) or a complement thereof.

in some embodiments, the kits provide a target-specific nucleic acid probe comprising at least a part of a single stranded sequence constituting one of the strands of a double stranded recognition site of a methylation-insensitive restriction enzyme. In some embodiments, the target-specific nucleic acid probe comprising at least a part of a single stranded sequence constituting one of the strands of a double stranded recognition site of a methylation-insensitive restriction enzyme comprises the sequence 5' CTA-CAACAATGGTCCAGGGAGCACA 3' (SEQ ID NO: 2) or a complement thereof.

In some embodiments, the kits provide a target-specific nucleic acid probe comprising a single stranded sequence lacking a recognition site for both a methylation-insensitive restriction enzyme and a methylation-sensitive restriction enzyme. In some embodiments, the target-specific nucleic acid probe comprising a single stranded sequence lacking a recognition site for both a methylation-insensitive restriction enzyme and a methylation-sensitive restriction enzyme comprises the sequence 5' TGAACCTGTGTCTGC-CACTGTGTG 3' (SEQ ID NO: 3) or a complement thereof.

In some embodiments, the kit comprises a mixture of target nucleic acid probes which comprises at least a first target nucleic acid probe and a second target nucleic acid probe and optionally a third target nucleic acid probe, wherein at least one of the probes comprises at least a part of a single stranded sequence, constituting one of the strands of a double stranded recognition site of a methylation-sensitive restriction enzyme.

Additionally or alternatively, the kits comprise one or more primer pairs selected from the group consisting of 5' AGGAGGAGCCTGAGAAGC 3' (SEQ ID NO: 4) and 5' CTTGTGTGCCTCTGCTGAG 3' (SEQ ID NO: 5); 5' CTGAGTGTGTGAACAAGCAGAG 3' (SEQ ID NO: 6) and 5' ACCTCATGCTGCTCTCCTTAG 3' (SEQ ID NO: 7); and 5' GGCTCAGCAAGTCTTCTGG 3' (SEQ ID NO: 8) and 5' CCTGGTGGGAAAGATGACC 3' (SEQ ID NO: 9).

In some embodiments, the kit comprises liquid medium containing the at least one target-specific nucleic acid probe in a concentration of 250 nM or less. With such a kit, the probes are provided in the required amount to perform reliable multiplex detection reactions according to the present technology. In some embodiments, the target-specific nucleic acid probes are detectably labeled.

In some embodiments, the kits further comprise buffers, methylation-sensitive and methylation-insensitive restriction endonucleases, enzymes having polymerase activity, enzymes having polymerase activity and lacking 5'→3' exonuclease activity or both 5'→3' and 3'5' exonuclease activity, enzyme cofactors such as magnesium or manganese, salts, chain extension nucleotides such as deoxynucleoside triphosphates (dNTPs) or biotinylated dNTPs, necessary to carry out an assay or reaction, such as amplification and/or detection of methylated target nucleic acid sequences in the MLH1 promoter.

In one embodiment, the kits of the present technology further comprise positive control methylated DNA sequences and negative control unmethylated DNA sequences to correct for any amplification variability between samples. A kit may further contain a means for determining the extent of methylation within the MLH1 promoter, and a means for comparing the extent of methylation with a standard. The kit may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kits of the present technology may include components that are used to prepare nucleic acids from a test sample for the subsequent amplification and/or detection of methylated target nucleic acid sequences in the MLH1 promoter. Such sample preparation components can be used to produce nucleic acid extracts from any bodily fluids (such as blood, serum, plasma, etc.) or from tissue samples. The test samples used in the above-described methods will vary based on factors such as the assay format, nature of the detection method, and the specific tissues, cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, and Applied Biosystems' PRISM™ 6700 sample preparation system.

EXAMPLES

Example 1: MLH1 Methylation Assay Design

FIG. 1 shows the nucleic acid sequences of the MLH1 promoter 'C' region, MLH1 intron 14, and ACTB amplicons, as well as the corresponding probe and primer sequences for each amplicon. The primers and probes of all three of the amplicons were designed to have very similar $T_m$ characteristics allowing them to function with similar efficiencies in the multiplex PCR reactions. Experiments that tested the efficiency of the primer pairs for each amplicon showed similarly high efficiencies for each amplicon (e.g., ~85-110%, usually around 95%), regardless of whether the PCR reaction was run singly or as a multiplex.

As shown in FIG. 1, the nucleic acid sequence of the MLH1 promoter 'C' region amplicon contains 2 recognition sites for the methylation-sensitive restrictive endonuclease HhaI, whereas the nucleic acid sequence of the MLH1 intron 14 amplicon contains 2 recognition sites for the methylation-insensitive restrictive endonuclease AluI. The target nucleic acid sequence at the exon 14-intron 14 junction of MLH1 was specifically selected as the internal control for enzymatic digestion in each test sample because of the enzymatic compatibility between the HhaI and AluI restriction enzymes. Both HhaI and AluI have 100% activity in CutSmart buffer, have an optimal incubation temperature of 37° C., and can be heat-inactivated at 95° C.

Additionally, no SNPs or COSMIC catalogued mutations were identified in either the MLH1 promoter 'C' region amplicon or the MLH1 intron 14 amplicon using UCSC Genome Browser, thereby eliminating a potential risk for false positive results.

The impact of high salt concentration of the restriction enzyme digests on the integrity of the MLH1 methylation assay of the present technology was also examined. Experiments that used QuantiTect MMX (Qiagen) buffer for the multiplex PCR reaction for a given sample (methylated or unmethylated) yielded Ct values that were similar to the Ct values obtained when the same sample was incubated with QuantiTect MMX (Qiagen) buffer and 1× CutSmart buffer. These results demonstrate that any differences observed when using higher salt concentrations are inconsequential and do not disrupt the ability of the assay to discriminate between methylated and unmethylated samples.

Example 2: Detection of Methylation of MLH1 Promoter 'C' Region in FFPE and Whole Blood Samples This Example demonstrates that the MLH1 methylation assay of the present technology can effectively discriminate between methylated and unmethylated samples, including FFPE tissues.

Genomic DNA was extracted from FFPE tissue or whole blood samples from CRC patients using standard protocols. The extracted DNA was quantified using the NanoDrop ND-1000 and dilutions for each sample were prepared according to the following guidelines:

| NanoDrop Quant (ng/µL) | Dilution | Prepare Dilution (need ≥ 5 µL): | Diluted Concentration (ng/µL) | Input DNA/Well (ng/well = 2 µL × diluted conc.) Target = 50-100 ng |
|---|---|---|---|---|
| 1-49 | None | N/A | 1-49 | 2-98* |
| 50-100 | 1:2 | 3 µL DNA + 3 µL H₂O | 25-50 | 50-100 |
| 101-200 | 1:4 | 2 µL DNA + 6 µL H₂O | 25-50 | 50-100 |
| 201-250 | 1:5 | 1 µL DNA + 4 µL H₂O | 40-50 | 80-100 |
| 251-500 | 1:10 | 1 µL DNA + 9 µL H₂O | 25-50 | 50-100 |
| 501-1000 | 1:20 | 1 µL DNA + 19 µL H₂O | 25-50 | 50-100 |

The "no enzyme" master mix was prepared as follows:

| | Final Concentration | x1 Rxn (µL) | x50 Rxn (µL) |
|---|---|---|---|
| CutSmart Buffer (10X) | 1X | 1 | 50 |
| H₂O (QuantiTect kit) | — | 7 | 350 |
| Total master mix: | | 8 | 400 |
| +DNA | 50 ng-100 ng | 2 | |
| Total reaction: | | 10 | |

The HhaI-AluI dual digest master mix was prepared as follows:

| | Final Concentration | x1 Rxn (µL) | x50 Rxn (µL) |
|---|---|---|---|
| CutSmart Buffer (10X) | 1X | 1 | 50 |
| HhaI enzyme (20 U/µL) | 5 U | 0.25 | 12.5 |
| AluI enzyme (10 U/µL) | 5 U | 0.5 | 25 |
| H₂O (QuantiTect kit) | — | 6.25 | 312.5 |
| Total master mix: | | 8 | 400 |
| +DNA | 50 ng-100 ng | 2 | |
| Total reaction: | | 10 | |

After preparing a "no enzyme" reaction and HhaI-AluI dual digest reaction for each sample in a 96-well PCR plate, the samples were incubated at 37° C. for 16 hours. The restriction enzymes were subsequently heat-inactivated at 95° C. for 20 minutes.

The master mix for the MLH1 multiplex PCR assay was prepared in a dead air box as follows:

| MLH1 Multiplex Master Mix Preparation | x1 Rxn (µL) | x28 Rxn (µL) | x100 Rxn (µL) | Final Concentration |
|---|---|---|---|---|
| QuantiTect 2X MMX Buffer | 10 | 280 | 1000 | 1X |
| MLH1 promoter 'C' region Primer/Probe Mix | 0.1 | 2.8 | 10 | Forward primer 200 nM Reverse primer 200 nM Probe 100 nM |
| MLH1 intron 14 Primer/Probe Mix | 0.13 | 3.64 | 13 | Forward primer 200 nM Reverse primer 200 nM Probe 250 nM |
| ACTB Primer/Probe Mix | 0.13 | 3.64 | 13 | Forward primer 200 nM Reverse primer 200 nM Probe 250 nM |
| Master Mix Total | 10.36 | 290.08 | 1036 | |

10.3 µL of prepared MLH1 multiplex master mix was added to each well of a LifeTech MicroAmp Fast Optical 96-well PCR plate. Following restriction digestion, the DNA samples were directly added to the wells containing the multiplex PCR master mix. The PCR plate was sealed with MicroAmp Optical Adhesive Film and transferred to the Viia™ 7 real-time PCR instrument.

The ultimate real-time quantitative PCR protocol employed is shown below:

| Enzyme Activation | 95°-20 min | 1 cycle |
|---|---|---|
| PCR | 95°-15 sec | 40 cycles |
| | 62°-30 sec | |
| | 72°-30 sec | |
| Cooling | 40°-10 sec | 1 cycle |

The real-time quantitative PCR data was analyzed using the Viia™ 7 software. MeScore calculations were performed using the formulas described herein.

Figure 3:
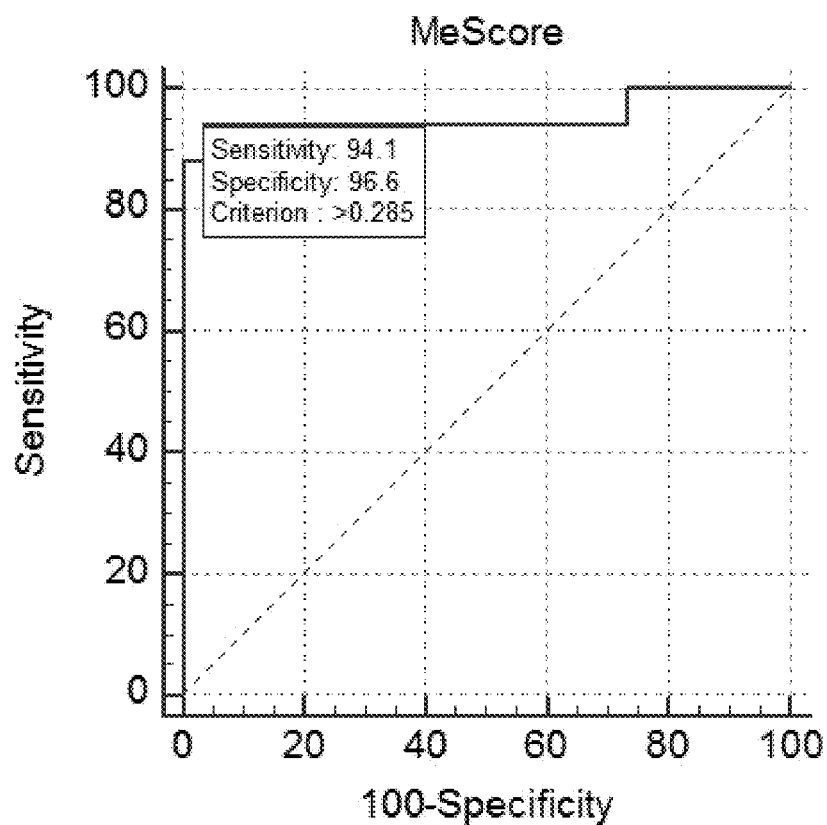
FIG. 3 is a Receiver Operating Characteristic (ROC) curve of the MLH1 methylation assay of the present technology, which plots the assay's true positive rate (sensitivity) against its false positive rate (100-Specificity) at different cutoff points for the "Methylation Score" (MeScore).
Figure 4A:
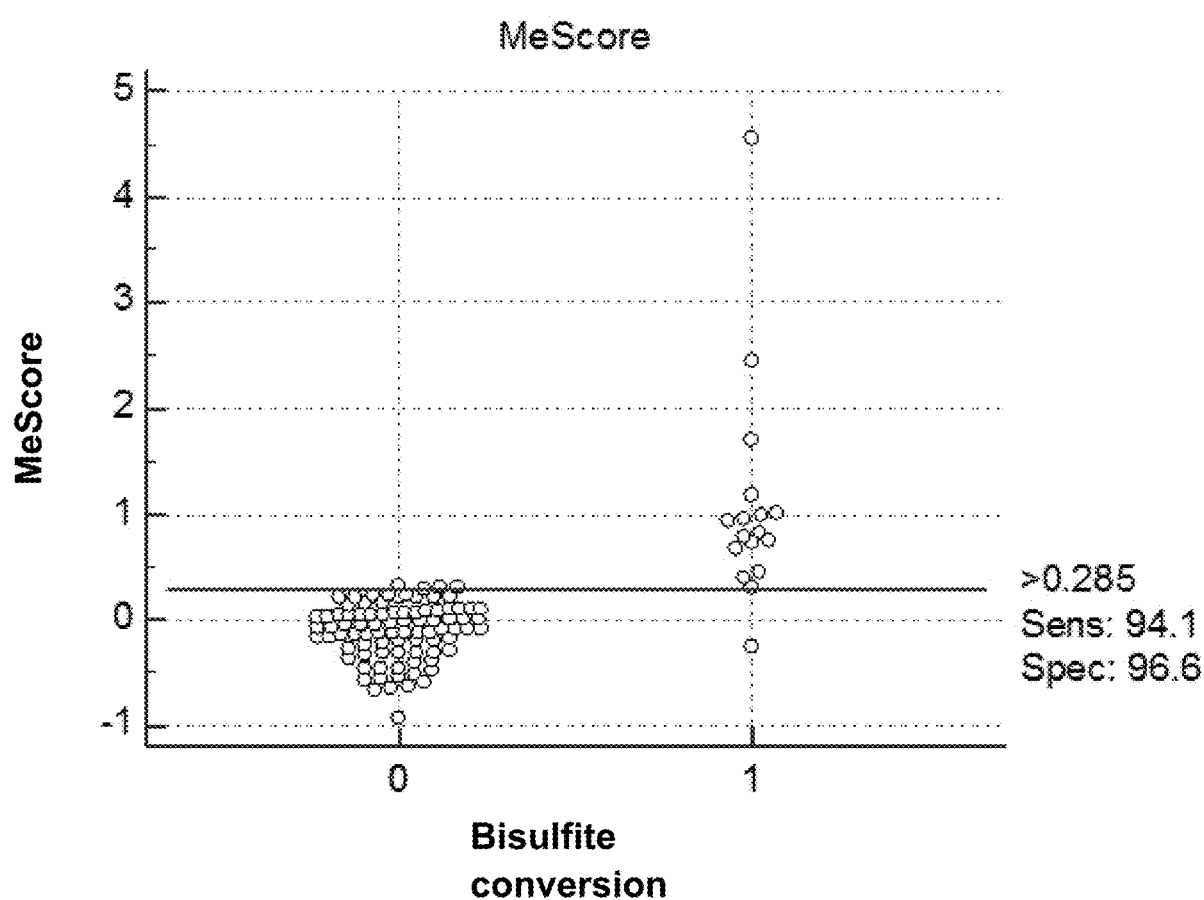
FIG. 4A shows a plot of the MeScore and corresponding bisulfite conversion data for each tested sample (n=104).

A MeScore >0.285 is considered positive for MLH1 promoter methylation, whereas a MeScore ≤0.285 is considered negative for MLH1 promoter methylation. The MeScore cut-off (which was calculated using the MedCalc Software) is based on the results of a validation study involving 104 samples that were tested using both the MLH1 methylation assay of the present technology, and a bisulfite conversion assay. FIG. 3 shows the ROC curve of the MLH1 methylation assay of the present technology, which was generated with the results of the bisulfite conversion validation study shown in FIGS. 4A and 4B. The predicted sensitivity and specificity of the MLH1 methylation assay of the present technology was 94.1% and 96.6% respectively at a threshold MeScore of >0.285.

Results. As shown in FIG. 2B, incubation with the methylation-insensitive enzyme AluI, which cleaves both unmethylated and methylated DNA, resulted in larger Ct values for the MLH1 intron 14 amplicon compared to the no enzyme control samples. In contrast, FIG. 2C shows that the Ct values for the ACTB amplicon of the dual digested samples were similar to the Ct values observed in the no enzyme control samples. FIGS. 2A and 2B show that the baseline enzymatic activity of HhaI on an unmethylated DNA control sample is comparable to that observed with AluI, as measured by the deltaCt between the no enzyme control and the digested samples (deltaCt=8.5 vs. 6.0 respectively). FIG. 2A also shows that the deltaCt values of the MSI+ FFPE samples were comparable to that observed in the methylated DNA control sample, thus demonstrating that the MLH1 promoter in these MSI+ samples was methylated.

The computed MeScore for each of the representative samples shown in FIGS. 2A-2C are shown below in Table 1. The observed variations in MeScore in the BRAF V600E+ and MSI+ CRC samples can be attributed to the heterogeneous nature of CRC FFPE samples, which may be due to partial methylation of the MLH1 promoter. The accuracy of the MeScore for the tested samples was independently confirmed via bisulfite conversion. As shown in Table 1, the overall concordance of the MLH1 MS-MLPA assay of the present technology (when compared to the bisulfite conversion results) is 93.75%.

Further, Table 2 demonstrates that the overall specificity for sample groups expected to be negative for MLH1 promoter methylation is 93%.

TABLE 2

| Sample Group (all expected to be negative for MLH1 promoter methylation) | N | MeScore algorithm-negative (≤0.285)* | Specificity for expected negative results |
|---|---|---|---|
| MSI+ matched "Normal" FFPE tissue | 11 | 9/11 | 82% |
| MSI-neg FFPE tumor tissue | 12 | 12/12 | 100% |
| MSI-neg matched "Normal" FFPE tissue | 9 | 8/9 | 89% |
| BRAF V600E-neg matched "Normal" FFPE tissue | 1 | 1/1 | 100% |
| Whole blood | 9 | 9/9 | 100% |
| Overall negative concordance | | 39/42 | 93% |

These results demonstrate that the MLH1 MS-MLPA assay of the present technology can detect methylation of the MLH1 promoter in FFPE tissue samples with high specificity and sensitivity. Therefore, DNA degradation and partial DNA denaturation during embedding of the tissues do not appear to influence the accuracy of the results of the MLH1 methylation assay of the present technology.

Accordingly, these results demonstrate that the MLH1 MS-MLPA assay of the present technology is useful for detecting aberrant methylation of the MLH1 promoter 'C' region in a sample. Further, these results demonstrate that the MLH1 MS-MLPA assay of the present technology is useful in methods for excluding Lynch syndrome as a possible diagnosis in a CRC or endometrial cancer patient.

TABLE 1

| | Sample Group | Samples | MLH1 promoter 'C' region dCt | MLH1 intron 14 dCt | ACTB dCt | Ratio C 1-(MLH1 promoter C dCt/MLH1 intron 14 dCt) | Ratio ACTB 1-(\|ACTB dCt\|/MLH1 intron 14 dCt) | MeScore Ratio C/Ratio ACTB | Bisulfite Result |
|---|---|---|---|---|---|---|---|---|---|
| Control | Negative control | UnMeDNA (100 ng) | 8.5 | 6.0 | -0.4 | -0.45 | 0.92 | -0.46 | neg |
| | Positive control | MeDNA (100 ng) | 0.1 | 5.1 | -0.1 | 0.98 | 0.97 | 1.01 | POS |
| Possible Methylation-Positive FFPE | MSI+ (FFPE) | 18121T | 0.019 | 1.8 | 0.0 | 0.99 | 0.99 | 0.99 | POS |
| | MSI+ (FFPE) | 139T | -0.8 | 1.8 | -1.2 | 1.47 | 0.32 | 4.56 | POS |
| | BRAF V600E+ (FFPE) | 12646 | 2.1 | 5.8 | 0.5 | 0.63 | 0.92 | 0.68 | POS |
| | MSI+ (FFPE) | 17191T | -0.5 | 1.1 | -0.5 | 1.47 | 0.60 | 2.44 | POS |
| | BRAF V600E+ (FFPE) | 13225 | 3.0 | 4.1 | 0.6 | 0.26 | 0.86 | 0.298 | POS |
| Likely Methylation-Negative FFPE or WB | Matched "N" of MSI-neg (FFPE) | 18122N | 2.3 | 3.3 | 0.2 | 0.29 | 0.93 | 0.32 | neg |
| | BRAF V600E-neg (FFPE) | 14634T | 1.9 | 2.4 | -0.2 | 0.19 | 0.91 | 0.21 | neg |
| | Matched "N" of BRAF V600E+ (FFPE) | 15844N | 3.7 | 4.0 | -0.2 | 0.08 | 0.95 | 0.08 | neg |
| | BRAF V600E-neg (FFPE) | 17544 | 4.9 | 3.1 | 0.2 | -0.59 | 0.95 | -0.63 | neg |
| | BRAF V600E-neg (FFPE) | 17213T | 5.4 | 3.8 | -0.4 | -0.42 | 0.89 | -0.47 | neg |
| | BRAF V600E-neg (FFPE) | 16997 | 2.7 | 2.3 | -0.1 | -0.16 | 0.96 | -0.17 | neg |
| | BRAF V600E-neg (FFPE) | 16489 | 1.8 | 1.6 | 0.4 | -0.11 | 0.75 | -0.15 | neg |
| | Matched whole blood of MSI-neg | 17191WB | 12.0 | 9.3 | -0.6 | -0.297 | 0.94 | -0.32 | neg |
| | Whole blood from JAK validation | 18671WB | 9.1 | 9.7 | -0.6 | 0.06 | 0.94 | 0.06 | neg |
| Concordance (provisional MeScore cutoff of POS > 0.285; see FIG. 4A) | | | | | | | | 15/16 concordant = 93.75% | |

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

---

The invention claimed is:

1. A method for detecting methylation of a target nucleic acid sequence in the promoter of MLH1 in a sample comprising
   (a) incubating the sample comprising double-stranded genomic DNA with at least one methylation-sensitive restriction enzyme and at least one methylation-insensitive restriction enzyme, wherein
      (i) the methylation-sensitive restriction enzyme and the methylation-insensitive restriction enzyme are not isoschizomers of each other;
      (ii) the methylation-sensitive restriction enzyme cleaves the double-stranded genomic DNA at unmethylated recognition sites for the methylation-sensitive restriction enzyme, leaving methylated recognition sites for the methylation-sensitive restriction enzyme intact;
      (iii) the methylation-insensitive restriction enzyme cleaves the double-stranded genomic DNA at both methylated and unmethylated recognition sites for the methylation-insensitive restriction enzyme;
      (iv) the target nucleic acid sequence in the promoter of MLH1 in the sample comprises a recognition site for the methylation-sensitive restriction enzyme; and
      (v) a target nucleic acid sequence at intron 14 of MLH1 in the sample comprises a recognition site for the methylation-insensitive restriction enzyme;
   (b) incubating the sample with a plurality of probes for querying a plurality of target nucleic acids in the sample, wherein the plurality of probes comprises
      (i) a first locus specific probe comprising a first target specific region complementary to the target nucleic acid sequence in the promoter of MLH1, wherein the sequence of the first locus specific probe is 5' AAGCACCTCCTCCGCTCTGC 3' (SEQ ID NO: 1) or a complement thereof and wherein the first locus specific probe is a single oligonucleotide; and
      (ii) a second locus specific probe comprising a second target specific region complementary to the target nucleic acid sequence at intron 14 of MLH1, wherein the second locus specific probe is a single oligonucleotide and wherein the first locus specific probe and second locus specific probe are detectably labelled;
   (c) hybridizing the plurality of probes to the plurality of target nucleic acids in the sample to form a plurality of hybridization complexes;
   (d) amplifying the plurality of hybridization complexes via real-time quantitative PCR to produce a plurality of amplicons, wherein amplification is carried out with a plurality of primer sets comprising
      (i) a first forward primer comprising a region that is complementary to a nucleic acid sequence located 5' from the target nucleic acid sequence in the promoter of MLH1;
      (ii) a first reverse primer comprising a region that is complementary to a nucleic acid sequence located 3' from the target nucleic acid sequence in the promoter of MLH1;
      (iii) a second forward primer comprising a region that is complementary to a nucleic acid sequence located 5' from the target nucleic acid sequence at intron 14 of MLH1; and
      (iv) a second reverse primer comprising a region that is complementary to a nucleic acid sequence located 3' from the target nucleic acid sequence at intron 14 of MLH1; and (e) detecting the plurality of amplicons, wherein detecting an amplicon comprising the target nucleic acid sequence in the promoter of MLH1 indicates methylation of the target nucleic acid sequence in the promoter of MLH1 in the sample,
wherein the methylation-sensitive restriction enzyme is HhaI.

2. The method of claim 1, wherein the plurality of probes further comprises a third locus specific probe comprising
a third target specific region complementary to a target nucleic acid sequence at ACTB, wherein the target nucleic acid sequence at ACTB does not contain a recognition site for the methylation-sensitive restriction enzyme and the methylation-insensitive restriction enzyme; and
wherein the third locus specific probe is a single oligonucleotide and is detectably labelled.

3. The method of claim 2, wherein the first locus specific probe, the second locus specific probe and the third locus specific probe are detectably labelled with distinct fluorophores.

4. The method of claim 3, wherein the fluorophores are selected from the group consisting of FAM, CY5 and HEX.

5. The method of claim 2, wherein the third locus specific probe comprises the sequence of 5' TGAACCTGT GTCTGCCACTGTGTG 3' (SEQ ID NO: 3) or a complement thereof.

6. The method of claim 2, wherein the plurality of primer sets further comprises
a third forward primer comprising a region that is complementary to a nucleic acid sequence located 5' from the target nucleic acid sequence at ACTB; and
a third reverse primer comprising a region that is complementary to a nucleic acid sequence located 3' from the target nucleic acid sequence at ACTB.

7. The method of claim 6, wherein the third forward primer comprises the sequence of 5' GGCTCA GCAAGTCTTCTGG 3' (SEQ ID NO: 8) and the third reverse primer comprises the sequence of 5' CCTGGTGG-GAAAGATGACC 3' (SEQ ID NO: 9).

8. The method of claim 1, wherein the second locus specific probe comprises the sequence of 5' CTACAA CAATGGTCCAGGGAGCACA 3' (SEQ ID NO: 2) or a complement thereof.

9. The method of claim 1, wherein the first forward primer comprises the sequence of 5' AGGAGGAGCCT-GAGAAGC 3' (SEQ ID NO: 4) and the first reverse primer comprises the sequence of 5' CTTGTGTGCCTCTGCT-GAG 3' (SEQ ID NO: 5).

10. The method of claim 1, wherein the second forward primer comprises the sequence of 5' CTGAGTGTGT-GAACAAGCAGAG 3' (SEQ ID NO: 6) and the second reverse primer comprises the sequence of 5' ACCT-CATGCTGCTCTCCTTAG 3' (SEQ ID NO: 7).

11. The method of claim 1, wherein the methylation-insensitive restriction enzyme is AluI.

12. The method of claim 1, wherein the sample is whole blood.

13. The method of claim 1, wherein the target nucleic acid sequence in the promoter of MLH1 corresponds to the MLH1 promoter 'C' region.

14. The method of claim 1, wherein the sample is derived from a subject diagnosed with colorectal or endometrial cancer.

15. The method of claim 14, wherein the subject diagnosed with colorectal or endometrial cancer is positive for BRAF V600E or microsatellite instability (MSI).

16. The method of claim 1, wherein the sample is derived from a subject suspected of having Lynch syndrome.

17. The method of claim 16, wherein the subject suspected of having Lynch syndrome displays tumors in one or more of colon, rectum, endometrium, stomach, ovary, urinary tract, and small intestine.

18. The method of claim 17, wherein the tumors of the subject suspected of having Lynch syndrome show a loss of MLH1 protein expression using immunohistochemical (IHC) methods.

19. The method of claim 17, wherein the tumors of the subject suspected of having Lynch syndrome are positive for MSI.

20. A method for excluding Lynch Syndrome as a possible diagnosis in a colorectal or endometrial cancer patient comprising
(a) incubating a sample comprising double-stranded genomic DNA with at least one methylation-sensitive restriction enzyme and at least one methylation-insensitive restriction enzyme, wherein
(i) the methylation-sensitive restriction enzyme and the methylation-insensitive restriction enzyme are not isoschizomers of each other;
(ii) the methylation-sensitive restriction enzyme cleaves the double-stranded genomic DNA at unmethylated recognition sites for the methylation-sensitive restriction enzyme, leaving methylated recognition sites for the methylation-sensitive restriction enzyme intact;
(iii) the methylation-insensitive restriction enzyme cleaves the double-stranded genomic DNA at both methylated and unmethylated recognition sites for the methylation-insensitive restriction enzyme;
(iv) a target nucleic acid sequence in MLH1 promoter in the sample comprises a recognition site for the methylation-sensitive restriction enzyme; and
(v) a target nucleic acid sequence at intron 14 of MLH1 in the sample comprises a recognition site for the methylation-insensitive restriction enzyme;
(b) incubating the sample with a plurality of probes for querying a plurality of target nucleic acids in the sample, wherein the plurality of probes comprises
(i) a first locus specific probe comprising a first target specific region complementary to the target nucleic acid sequence in MLH1 promoter, wherein the sequence of the first locus specific probe is 5' AAGCACCTCCTCCGCTCTGC 3' (SEQ ID NO: 1) or a complement thereof and wherein the first locus specific probe is a single oligonucleotide; and
(ii) a second locus specific probe comprising a second target specific region complementary to the target nucleic acid sequence at intron 14 of MLH1, wherein the second locus specific probe is a single oligonucleotide and wherein the first locus specific probe and second locus specific probe are detectably labelled;
(c) hybridizing the plurality of probes to the plurality of target nucleic acids in the sample to form a plurality of hybridization complexes;
(d) amplifying the plurality of hybridization complexes via real-time quantitative PCR to produce a plurality of amplicons, wherein amplification is carried out with a plurality of primer sets comprising
(i) a first forward primer comprising a region that is complementary to a nucleic acid sequence located 5' from the target nucleic acid sequence in MLH1 promoter;

(ii) a first reverse primer comprising a region that is complementary to a nucleic acid sequence located 3' from the target nucleic acid sequence in MLH1 promoter;
(iii) a second forward primer comprising a region that is complementary to a nucleic acid sequence located 5' from the target nucleic acid sequence at intron 14 of MLH1; and
(iv) a second reverse primer comprising a region that is complementary to a nucleic acid sequence located 3' from the target nucleic acid sequence at intron 14 of MLH1; and (e) detecting an amplicon comprising the target nucleic acid sequence in MLH1 promoter and identifying the patient as not suffering from Lynch Syndrome, wherein the methylation-sensitive restriction enzyme is HhaI.

* * * * *